(12) United States Patent
Streit et al.

(10) Patent No.: US 6,495,097 B1
(45) Date of Patent: Dec. 17, 2002

(54) FRAGRANCE AND FLAVOR COMPOSITIONS CONTAINING ODOR NEUTRALIZING AGENTS

(75) Inventors: Allan L. Streit, Sparta, NJ (US); Harry Hayes, Hampden, MA (US); Grant Mudge, West Redding, CT (US)

(73) Assignee: Shaw Mildge & Company, Shelton, CT (US)

( * ) Notice: Subject to any disclaimer, the term of this patent is extended or adjusted under 35 U.S.C. 154(b) by 0 days.

(21) Appl. No.: 10/085,605

(22) Filed: Feb. 27, 2002

Related U.S. Application Data

(63) Continuation of application No. 09/515,475, filed on Feb. 29, 2000, now abandoned.
(60) Provisional application No. 60/122,438, filed on Mar. 2, 1999.

(51) Int. Cl.$^7$ .................................................. A61L 9/01
(52) U.S. Cl. ..................... 422/5; 422/120; 424/76.21; 424/76.4; 424/76.6; 424/76.8; 424/65
(58) Field of Search ................. 422/4, 5, 120; 424/76.2, 76.4, 76.8, 78.31, 76.21, 76.6, 65

(56) References Cited

U.S. PATENT DOCUMENTS

| | | |
|---|---|---|
| 3,193,451 A | 7/1965 | Reinisch et al. |
| 4,517,919 A | 5/1985 | Benjamin et al. ............... 119/1 |
| 5,209,932 A | 5/1993 | Nichols ....................... 424/409 |
| 5,275,783 A | 1/1994 | Menassa et al. ................. 422/5 |
| 5,338,511 A | 8/1994 | Menassa et al. ................. 422/5 |
| 5,439,641 A | 8/1995 | Caupin et al. .................. 422/5 |
| 5,500,138 A | 3/1996 | Bacon et al. ................. 252/8.8 |
| 5,531,910 A | 7/1996 | Severns et al. ............. 510/102 |
| 5,539,034 A | 7/1996 | Caupin et al. ............... 524/315 |
| 5,652,206 A | 7/1997 | Bacon et al. ................. 510/101 |
| 5,668,102 A | 9/1997 | Severns et al. ............. 510/504 |
| 5,720,947 A | 2/1998 | Basset et al. ............... 424/76.1 |
| 5,780,020 A | 7/1998 | Peterson et al. .............. 424/65 |
| 5,885,599 A | 3/1999 | Peterson et al. ............ 424/405 |
| 5,976,460 A | 11/1999 | Bourson et al. ................. 422/5 |

FOREIGN PATENT DOCUMENTS

| | | |
|---|---|---|
| AU | 651 433 B | 7/1994 |
| EP | 0 781 562 | 7/1997 |
| FR | 2 744 992 A | 8/1997 |
| FR | WO 00 35498 A | 6/2000 |
| GB | 2 091 553 A | 8/1982 |
| GB | WO 98 29608 A | 7/1998 |
| WO | WO 93 07853 A | 4/1993 |

*Primary Examiner*—Elizabeth McKane
(74) *Attorney, Agent, or Firm*—St. Onge Steward Johnston & Reens, LLC

(57) ABSTRACT

A composition and a method of use for reducing malsensory agents comprising a component selected from the group consisting of fragrances, flavors, unfragranced carriers and mixtures thereof, with undecylenic acid and/or a derivative thereof, in an amount effective to reduce the malsensory agents and allow release of the component from the composition.

17 Claims, 7 Drawing Sheets

FRAGRANCE AND FLAVOR COMPOSITIONS CONTAINING ODOR NEUTRALIZING AGENTS

PRIORITY APPLICATION

This application is a Continuation Application of U.S. patent application Ser. No. 09/515,475, filed Feb. 29, 2000 now abandoned and claims the benefit of provisional application No. 60/122,438, filed Mar. 2, 1999.

FIELD OF THE INVENTION

The present invention relates to a composition and method for using the composition to neutralize or reduce malodors and bad tastes. More particularly, the present invention is directed to the use of undecylenic acid, its esters and/or salts, with fragrance and flavor components, and in products containing same to provide for odor neutralization of undesired aromas and tastes while maintaining the effect of the fragrance and flavor components. The composition of the present invention comprises undecylenic acid, its esters and/or salts with desirable fragrances and flavors at such concentrations that scavenging of the desirable volatilized fragrance and flavor components are minimized while maintaining an effective scavenging activity for undesired aromas and tastes. The present invention finds application in a wide variety of products such as, but not limited to, fabric and linen spray, candles, carpet deodorizer, hand sanitizer gels, room sprays and oral care products such as dentrifices and mouth washes.

BACKGROUND OF THE RELATED ART

Fragrances and flavors are often used to provide sensory aesthetic benefits. Release of a particular fragrance and/or flavor from a composition can serve as a signal that the composition is not fouled or ineffective, or may be associated with particular attributes such as a strength, cleanliness and usefulness. Fragrances and flavors are added to numerous consumer products to provide sensory signals indicating the quality and worth of the product.

The practical use of a composition may be limited due to fouling of the composition with undesirable contaminants, break-down products, or other materials which produce undesired aromas and tastes ("malsensory agents"). While prevention of the formation of malsensory agents may be deemed preferable, and may be practicable in certain circumstances, such as when antibacterial or antifungal agents are used to reduce the number of microorganisms which excrete malsensory agents, often it is not possible to prevent fouling of a composition used in an environment exposed to malsensory agents.

Undesired aromas and tastes in a composition may be ameliorated by chemical modification of the malsensory agent (e.g., by reacting it with reactant so as to produce a new composition, such as an adduct or further breakdown product which lacks an undesired aroma and/or taste), reducing the release of the malsensory agent from the composition (as by absorption and/or adsorption of the malsensory agent onto another compound such as charcoal or zeolites), reducing the vapor pressure of the malsensory agent (making it less volatile), or by removal of the malsensory agent from the composition (as by solvent extraction). Undesired aromas and tastes may also be ameliorated by judicious use of fragrances and/or flavors in amounts sufficient to mask the malsensory agent.

Numerous compounds, which range from non-descript plant extracts to single and multiple chemical entities, have been touted to reduce the sensory perception of malodors. For example, U.S. Pat. No. 3,923,005 to Fry et al. discloses the use of chlorophyll to remove the smell from used cat litter, while U.S. Pat. No. 4,989,727 discloses a deodorant consisting of deodorizing ingredients extracted from plants said to be useful for a wide variety of smells including sulfur and nitrogen compound odors.

U.S. Pat. No. 4,909,986 to Kobayashi et al., discloses compounds useful as deodorants including water-soluble organic polymers having an average molecular weight of at least 100,000.

U.S. Pat. No. 4,959,207 to Ueda et al. discloses a mixture of an undecylenic acid anhydride with a copper compound.

U.S. Pat. No. 3,091,511 to Calhoun discloses a salicylic undecylenic acid ester of phenol and p-acetylaminophenol.

U.S. Pat. No. 5,718,887 to Wolf et al., discloses Ω-alkanedicarboxylic acids and moncarboxylic acid-esters of oligoglycerols as useful in reducing body odor, and U.S. Pat. No. 5,534,165 to Pilosof et al. discloses beta-cyclodextrin as a deodorant.

Among the many compounds said to have deodorizing activity are undecylenic acid and its derivatives. Undecylenic acid ($C_{11}H_{20}O_3$) is a naturally occurring acid found in tears and sweat. It is commonly derived from cracking $C_{18}$, often derived from castor oil, into $C_7$ and $C_{11}$ (where $C_{11}$ is known as undecylenic acid or undecanoic acid).

Undecylenic acid and its derivatives display interesting biological profiles which have been used in such diverse products as pediculicides (See, e.g., U.S. Pat. No. 5,416,116) and wild game repellants (to protect against the damage of crops—See, e.g., DE-A-1,792,467). Initially undecylenic acid was proposed as a deodorizing agent based on its bacteriostat (See, e.g., U.S. Pat. No. 3,762,875) and fungistat activities (See, e.g., U.S. Pat. Nos. 3,882,868, 3,899,616 and 4,462,981) where bacterial and fungal break-down products are frequently malsensory in nature. Later it was recognized that undecylenic acid, and a number of its derivatives are effective deodorizing agents in and of themselves.

Undecylenic acid has been used as deodorant in several products, including animal litter boxes (See, e.g., U.S. Pat. No. 4,517,919 which discloses the use of undecylenic acid in a flexible absorbent pad for use in animal litter boxes). It has also been used in conjunction with other deodorizing agents to enhance deodorization. For example, U.S. Pat. No. 5,182,103 discloses undecylenic acid, among many other compounds, to be useful in combination with an aluminometasilicate coated composite to provide an improved deodorant for refrigerators, garbage cans, automobiles, leather insole for shoes, paper diapers, menstrual products and general in-room use.

Ester derivatives of undecylenic acid, in particular, have been found to possess significant deodorizing activity. Polyoxyalkylene and simple alkyl esters of undecylenic acid have been found to be quite useful in the treatment of animal excreta. For example, U.S. Pat. No. 5,275,783 discloses the use of polyoxyalkylene esters of undecylenic acid as useful for the deodorization of liquid manures, while U.S. Pat. No. 5,338,511 discloses the use of alkyl and polyoxyalkylene ester derivatives of undecylenic acid at a concentration on the order of 0.01% to 5% by weight as useful in the deodorization of sewage sludges. See also, U.S. Pat. No. 5,720,947 disclosing the use of undecyleneic acid, its esters and its polyoxyalkylenated esters in conjunction with superphosphates in the deodorization of animal excreta. Such ester derivatives have also found use in the deodorization of paper mill effluents (See, U.S. Pat. No. 5,439,641), the removal of odors from malodorous animal foodstuffs (See, U.S. Pat. No. 5,747,090 and EP-0-434-524 which disclose deodorization with an alkyl or polyoxyalkylene ester of undecylenic acid, and its methyl, propyl, hexyl and decyl ester derivatives), and the deodorization of paper products, cardboards and non-woven material, such as found in filters, vacuum cleaner bags, nappies and air freshener diffusers (See, U.S. Pat. No. 5,976,460). Use of undecylenic acid ester derivatives in conjunction with polyetheresteramide polymers as deodorants is also disclosed in European Patent Application Publication No. 0 596 772.

It is believed that undecylenic acid, and its derivatives, deodorize by forming an extended conjugated system that reduce the vaporization of malsensory agents thereby reducing the density of such agents in the gaseous phase by amounts detectable by the human olfactory receptors. This can be confirmed as shown by a decrease of the density of the agents in the gaseous phase by sophisticated analytical techniques, including gas chromatography and mass spectroscopy. It was generally believed that intimate contact created for example, by physical mixing or spraying between the undecylenic acid, or its derivatives, and the malodor producing agent is necessary in order for a reduction in malodor to occur.

The deodorizing action of undecylenic acid and its ester derivatives appears to be independent of the inherent aroma of the particular undecylenic acid derivative. For example, methyl undecylenate, a known carnation base (See, U.S. Pat. Nos. 4,137,677 and 4,250,001), and ethyl undecylenate, characterized by some as an "enduring perfume ingredient", that is an ingredient that will remain on a fabric or body (as the case may be) throughout any rinse and drying steps (See, e.g., U.S. Pat. Nos. 5,500,137, 5,500,138, 5,500,154, 5,531,910, 5,790,404, and 5,849,310), as well as an "alcohol masking" agent (See, U.S. Pat. No. 5,843,881), both reduce perception of malodors to a far greater extent than can be associated with any masking of the malodors by any aroma of the respective undecylenate ester.

Application of undecylenic acid derivatives has conventionally been limited to removing odors from non-consumable substances, such as sludges, personal care products, paper products and animal feeds. While many undecylenic acid derivatives are non-toxic, such acids and their derivatives have not been used to reduce mal-tasting flavors in human-consumed foodstuffs and expectorants (such as mouthwashes and dentifrices).

While undecylenate derivatives and their salts are quite effective at reducing malodors, they all suffer from a major disadvantage in that they are thought to scavenge both malodors and desired odors, such as perfumes and flavoring agents, without selectivity.

Therefore, there is a need for a composition and method that makes use of the advantageous malodor neutralizing and retention properties of undecylenic acid, its esters, and salts thereof, without disadvantageously affecting the release of desired aromas and flavors or negatively effecting the end use hedonics of such.

SUMMARY OF THE INVENTION

The present invention provides fragrance and flavor compositions containing malsensory agent neutralizing compositions for inclusion in a variety of consumer products. In particular, by pre-mixing the neutralizing composition with the fragrance at a defined ratio, the present invention provides fragrance and flavor compositions that permit enhanced neutralization of malsensory agents while permitting advantageous controlled release of the desired fragrance and/or flavor. The present invention further provides for prolonged release of fragrances, and without any undesirable aromas that may be associated with the undecylenic acid and/or its derivatives.

The composition and method of the present invention reduces undesirable scavenging of fragrances and flavors in products incorporating undecylenic acid, and its derivatives, by pre-mixing the undecylenic acid and/or its derivatives with fragrances and flavor agents in a medium such that the concentration of the undecylenic acid and/or its derivatives is from about 5% to about 50% by weight of the medium for the pre-mix, and then adding the resultant pre-mix medium to products or carriers which are desired to be deodorized or used for deodorization. Pre-mixture of the undecylenic acid and its derivatives with the desired fragrances and flavors at such concentrations has also been found to provide a composition with improved release of the fragrance and/or flavoring agent over time. What is meant herein by a composition with improved release of fragrance and/or flavoring components is a composition using undecylenic acid, and/or its derivatives with fragrance and/or flavor components wherein the release of many of the flavor and/or fragrance components is controlled over a time period that is longer than without the composition. This is most advantageous where greater fragrance longevity is desirable, while minimizing substantial diminution of fragrance or flavor impact or strength.

The present invention also produces the unexpected results where undecylenic acid, and its derivatives, in particular its ester derivatives, are useful for removing odors even in a non-aqueous environment. In particular, the unexpected results are that undecylenic acid, its esters and salts, and other derivatives, remain effective in removing odors even when allowed to volatilize into the air without mechanical assistance (i.e. spraying), or intimate contact. When formulated into a spray product, and directed onto fabric materials, undecylenic acid, and its derivatives, have unexpectedly been found to provide significantly better effectiveness in removing common place odors, such as tobacco smoke smell, feces odors, cooking smells, body odors and feminine odors than commonly used cyclodextrins (See, e.g., U.S. Pat. Nos. 5,534,165, 5,714,137, 5,668,097, 5,783,544, 5,942,217, 5,968,404). Particularly improved performance was seen with fragrance compositions for a pre-mix including about 5% to about 50% of undecylenic acid and/or it derivatives, more preferably wherein the pre-mix comprises 10–30% of a mixture of about 60–90% ethyl undecylenate with about 10–40% methyl undecylenate, the balance of the pre-mix containing fragrance and/or flavor component(s). The improved odor neutralizing performance of the pre-mix was also observed when used in a concentration of about 0.5–2.0% by weight in a fabric spray comprising, for example, about 0–40% alcohol, 0.2–10% surfactant, the balance being water. The specific combination of methyl and ethyl undecylenates allowed for the lower odor inherent in the ethyl undecylenate, and the greater efficacy of the methyl component at a low enough level so as to minimize its own solvent-like odor contribution, and obtain optimal malodor neutralization.

The use of compositions containing undecylenic acid and its derivatives in particular, the methyl and ethyl esters thereof, was unexpectedly determined to remove odors from the atmosphere in which such compositions were burned or heated, as in products that can maintain a flame, or products which utilize other dynamic energy sources. In addition, vaporization of the undecylenic acid, and its derivative, in particular the methyl and ethyl esters thereof, into the atmosphere was seen to remove malodors dispersed in such atmosphere even though the undecylenic acid/acid-derivatives were not in direct contact with the source producing the odor.

Particularly useful odor neutralizing agents were found to include undecylenic acid, salts of undecylenic acid (e.g., sodium, calcium and zinc), simple esters of undecylenic acid (e.g., methyl, ethyl, propyl, butyl), undecylenate silicone esters, and combinations of undecylenic acid esters.

DETAILED DESCRIPTION OF THE INVENTION

Figure 1:
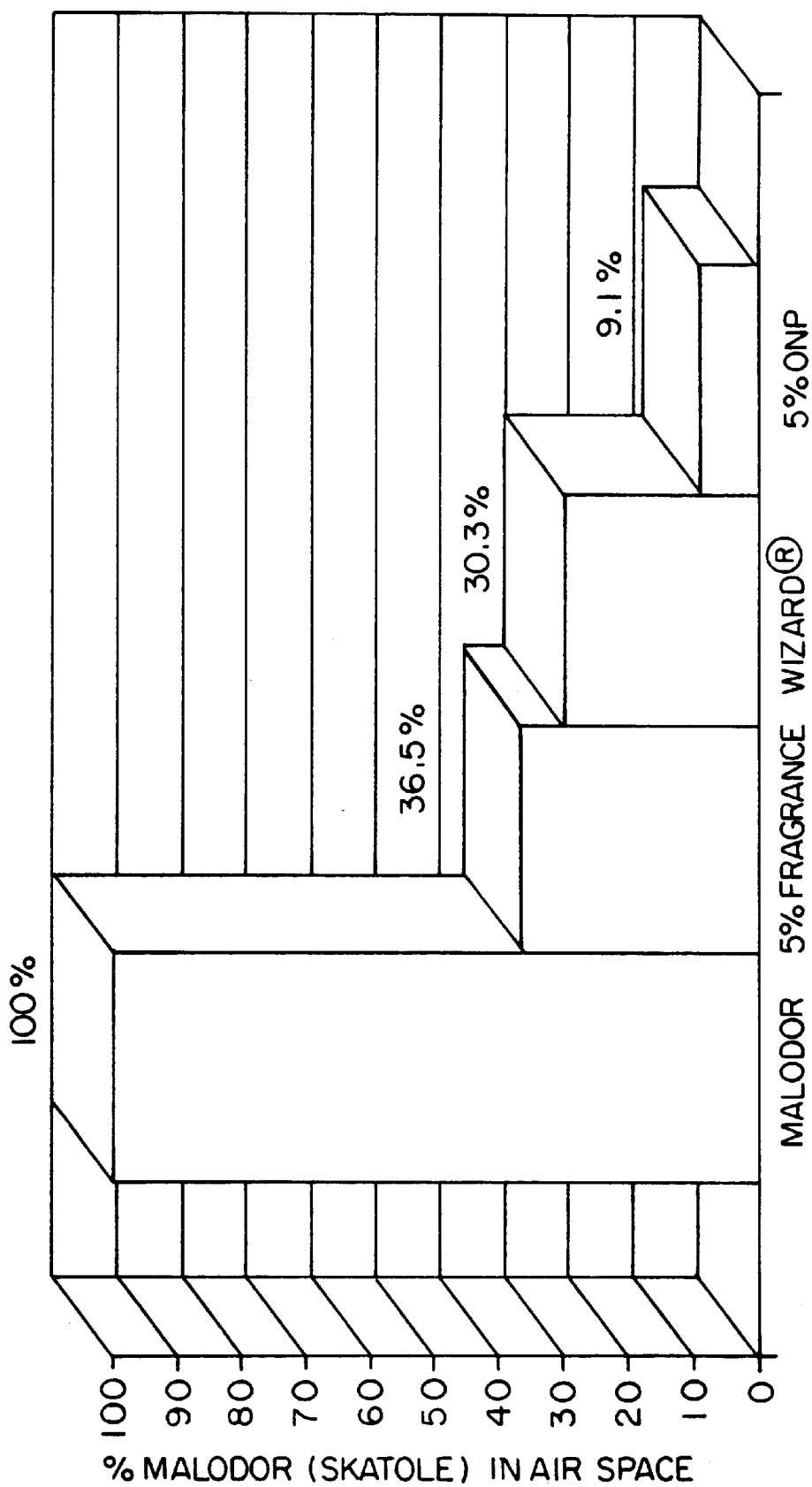
FIG. 1 graphically shows the reduction in malodor (skatole) detected in the air space after treatment with the composition of the present invention embodied in candles tested in Example 1.

The present invention provides an improved composition and method for removing malsensory agents from solids, fluids, and gases. There is provided fragrance and flavor compositions containing undecylenic acid derivatives which remove many common place odors including tobacco smoke, body odor, fecal and urine odors, food and cooking smells as well as "bad breath " agents such as various sulfides and sulfur mercaptans.

In one embodiment, undecylenic acid is used in its methyl and/or ethyl ester form. Preferably, the undecylenic acid/derivative is pre-mixed with a fragrance or flavor component in a solution to form a odor neutralizing "pre-mix" or "ONP" such that the final composition of the finished product contains less than about 50% w/w, but more than about 0.1% w/w, undecylenic acid and/or its derivative. Alternatively, the undecylenic acid/derivative may be contained in an unfragranced carrier. It is also understood that the ONP may be prepared by pre-mixing a fragrance, flavor, or unfragranced carrier component in a solution in any order with the undecylenic acid and/or derivative to form the "pre-mix." Preferably, the undecylenic acid and/or its derivative comprises less than about 30% w/w, but more than about 5% w/w, of the pre-mix composition. As an example and not as limitation to present invention, the pre-mix can be added to a carrier substrate, composition, or item from which an odor or mal-flavor is to be removed to form a finished product, such that the pre-mix comprises between about 0.1–100% w/w of the finished product. Such compositions have been shown to significantly reduce the olfactory perception of numerous compounds including, without limitation, 3-methyl-2-hexanoic acid (found in perspiration), caproic acid (found in rancid butter), skatole (an odorous component of feces), and methyl sulfide (a smell produced by rotten eggs). Unexpectedly, it has been found that too high concentrations (typically in excess of 30–50%) of the undecylenic acid and/or its derivatives in the pre-mix may actually adversely affect perceptions of odor and taste hedonics such that the pre-mix is ineffective in improving acceptability of the composition or item.

In another embodiment, the undecylenic acid and/or a derivative thereof is incorporated into a product which can maintain a flame, such as a candle. In another embodiment, undecylenic acid is used in its methyl and/or ethyl ester form. The undecylenic acid and/or its derivatives is pre-mixed with the fragrance or flavor blend such that the final product or composition contains less than about 50% w/w, but more than about 0.1% w/w, undecylenic acid and/or a derivative thereof. Preferably, the fragrance or flavor pre-mix comprises less than 20% w/w, but more than about 2% w/w, of the final product or composition. A preferred concentration of the undecylenic acid, or derivative thereof, is in the range 0.1%–4.0% w/w of the final product or composition. Unexpectedly, it has been found that undecylenic acid and its ester derivatives can be released from a burning candle in a form such that malodors, such as skatole, cooking odors or cigarette odors can be removed from the atmosphere without mechanical assistance such as spraying, mixing, filtration, electrostatic precipitation, or the like.

It is understood that the composition and method of the present invention is not restricted to any particular physical mode or product form, and may be contained for example and not as the limitation to the present invention, in aqueous and non-aqueous products, foams, powders, granules, gels, aerosols, non-aerosols, ceramics, blotters, waxes, microencapsulated vehicles, phase-change microencapsulated vehicles, plastics, polymers, non-wovens, inert carriers (i.e., silicates), and the like. The composition and method of the present invention may be used in a number of product applications, for example and not as a limitation to the present invention, carpet care, bathroom care, baby care, deodorants, antiperspirants, feminine hygiene products, room fresheners, air fresheners, candles, pet care, adult incontinence products, hand deodorizers/sanitizers, fabric/laundry care, oral hygiene products, household cleaning products, colognes, perfumes, hair care products, air conditioning/residential/industrial heating applications, hand surface cleaners, wipes, breath fresheners, depilatories, insecticides and repellents, and the like.

Preferred concentrations for the composition of the present invention are shown in following tables based on weight percentage.

TABLE A

Oder Neutralizng Pre-Mix (ONP)

| | Acceptable Range (wt. %) | Preferred Range (wt. %) |
|---|---|---|
| Fragrance | 50–95% | 70–90% |
| Undecylenic Acid and/or Derivative | 5–50% | 10–30% |

Table A lists the acceptable and preferred ranges associated with the pre-mix composition of the present invention, that is before the pre-mix may be diluted into a finished product.

TABLE B

Finished Product

| | Acceptable Range (wt. %) | Preferred Range (wt. %) |
|---|---|---|
| Pre-Mix | 0.1–100% | 2–20% |
| Undecylenic Acid and/or Derivative | .005–50% | 0.1–20% |

Table B lists the acceptable and preferred ranges associated with the composition of the present invention for the finished product.

TABLE C

Breakdown of Undecylenate in Pre-Mix Before Fragrance is Added

| | Acceptable Range | Preferred Range |
|---|---|---|
| Methyl Undecylenate | 0–100% | 5–30% |
| Ethyl Undecylenate | 0–100% | 70–95% |

Table C lists the acceptable and preferred ranges associated with methyl and ethyl undecylenate for the pre-mix when analyzed without addition of any fragrance and/or flavor component being added thereto. In this respect, acceptable and preferred ratios between methyl and ethyl undecylenate in the pre-mix and ultimate finished product are disclosed.

The following examples illustrate the preparation and use of the composition of the present invention. The examples are presented to further illustrate and explain the present invention and should not be taken as limiting in any regard. Unless otherwise indicated in the examples, and elsewhere in the specification or claims, all parts and percentages are by weight. Temperatures are degrees Centigrade. As would be obvious to one of ordinary skill in the art, a wide variety of aqueous, non-aqueous product formulations and applications extending beyond the examples set forth below would benefit from the inclusion of such active agents. In addition, it would be obvious to one of ordinary skill in the art that various forms of the described fragrances and flavors may be employed, for example, such as blotters, ceramics, microencapsulation, gelling, and the like.

To accurately determine the quantitative performance of the invention, head space analysis may be performed by any of the techniques known in the art including purge-and-trap concentration of volatiles, liquid-liquid extraction, solid phase extraction, or supercritical fluid extraction for semi-volatiles and non-volatiles. A technique known to those skilled in the art as "Solid Phase Micro Extraction" ("SPME") is used to sample the head space (i.e., the gaseous phase above the sample comprising the volatile components which make up the odor or aroma of the test sample). In SPME, analytes establish equilibria among the sample matrix, the headspace above the sample and a stationary phase of a fused silica fiber coated with a carbowax, polyacrylate or polydimethylsiloxane phase (these phases can be mixed with solid adsorbents, e.g., divinylbenzene polymers, template resins or porous carbons). The fiber is typically attached to a stainless steel plunger in a protective holder. Analytes are then thermally desorbed from the fiber to a gas chromatography column HPLC or GC/MS. As no solvent is injected, the analytes are rapidly desorbed, and the minimum detection limit of the analyte and resolution thereof is improved. Combined gas chromatography (GC) and mass spectroscopy (MS) can be used to analyze the sample headspace. The GC separates the mixture into its individual components and the MS detects these components as they emerge from the end of the GC column. In MS, the analyte molecules are fragmented by a high energy stream of electrons which results in some analyte molecules ionized to a positive charge. The charged ions are then separated according to mass, counted and plotted versus intensity to provide a mass spectrum. Such a technique provides a very accurate representation of the odor profile and character results.

The head space analysis shown in the following examples is obtained with an HP 6890 GC fitted with an HP 5973 Mass Spectrometer apparatus by using a 10 micro-liter syringe to remove an injection volume of about 0.2 micro-liters from the sample headspace and manually injecting it into the apparatus. Column and selection settings are chosen to maximize the detection of the compound being sought. A Supelco 2-4040 polydimethyl siloxane capillary column SPB-1 (60 meter length, 250 mm diameter, 0.25 mm film) is used. An initial oven setting of 80 deg C. (with a 4 minute ramp) and final temperature of 260 deg C. (with the 15 minute ramp) is used. A front inlet operated in a splitless mode with an initial temperature of 230 deg C., pressure 15.3 psi, and a purge flow 92.4 ml/min, for a total flown of 95.5 ml/min is used in the analysis of a number of malodors.

The following data was analyzed using an HP Vectra XM Series 4, 5/166 Chem Station and comparisons were made between each of the test cells.

Table 1 A represents a list of the constituents with their CAS# (Chemical Abstract Service number) for the fragrance component used in EXAMPLE 1.

TABLE 1A

| COMPONENT | CAS # | % |
|---|---|---|
| Aldehyde C-16 | 000077-83-8 | 000.730 |
| Allyl caproate FCC | 000123-68-2 | 000.100 |
| Benzyl acetate | 000140-11-4 | 000.580 |
| Benzyl benzoate | 000126-51-4 | 077.840 |
| Benzyl cinnamate | 000103-41-3 | 000.030 |
| Cinnamic alcohol | 000104-54-1 | 000.260 |
| Ethyl benzoate | 000093-89-0 | 000.040 |
| Ethyl butyrate | 000105-54-4 | 000.370 |
| Ethyl maltol | 004940-11-8 | 000.120 |
| Ethyl propionate | 000105-37-3 | 000.350 |
| Ethyl vanillin | 000121-32-4 | 000.410 |
| Hercolyn d | 008050-15-5 | 010.000 |
| Ionone beta pure | 014901-07-6 | 000.200 |
| Cis-3-hexenol | 000928-96-1 | 000.020 |
| Veltol | 000118-71-8 | 000.100 |
| Methyl anthranilate | 000134-20-3 | 000.980 |
| Methyl cinnamate | 000103-26-4 | 000.480 |
| Methyl isoeugenol | 000093-16-3 | 001.850 |
| Oxanone crystals | 005471-51-2 | 003.490 |
| Vanillin nf fcc | 000121-33-5 | 000.480 |
| Gamma-undecalactone | 000104-67-6 | 000.280 |
| Ionone alpha regular | 000127-41-3 | 001.010 |
| Beta-damascone | 023726-92-3 | 000.030 |
| Ethyl lactate | 000097-64-3 | 000.250 |
| Total | | 100.000 |

EXAMPLE 1

Effectiveness of Odor-Neutralizing Agents Incorporated into Candle Wax in Combination with Fragrance Against Skatole Odorant in Ambient Atmosphere when the Candle is Burned An odor-neutralizing pre-mix ("ONP") is prepared containing 80 parts by weight of components according to Table 1A and further containing 20 parts by weight of undecylenate wherein the undecylenate consists of 25% methyl undecylenate and 75% ethyl undecylenate. The ONP is then added to paraffin and subsequently fabricated into a candle, such that the ONP comprised 5% w/w of the candle wax. Paper blotters containing 4 grams of a 10% w/w solution of skatole in ethyl alcohol are placed into four chambers and allowed to stand for 30 minutes providing a malodor control test case. In each of the three other chambers the following candle formulations were placed alongside the paper blotters in each test chamber; a candle having 5% fragrance according to Table 1A; a candle having 5% ONP with undecylenate; and as an odor control candle benchmark a WIZARD DUAL ACTION CRISP BREEZE® brand candle as manufactured by Reckitt Benckiser of Wayne, N.J. Each of the candles are burned for 30 minutes, and the air space in the chambers is then analyzed. As shown in Table 1B and FIG. 1, the candle comprising 5% w/w of the ONP provided superior malodor protection.

TABLE 1B

| Test Case | Percent of Skatole Detected in Air Space |
|---|---|
| Malodor Control | 100% |
| 5% fragrance | 36.53% |
| Wizard ® Brand Candle | 30.29% |
| 5% ONP with undecylenate | 9.07% |

The following analysis contained in Table D is typical of the carrier solution used to dilute the odor neutralizing pre-mix (ONP) to a desired weight percentage used as a fabric spray.

TABLE D

| COMPONENT | % |
|---|---|
| Liposorb I-29 (Lipo Chemical) | 001.00 |
| Kathon CG/ICP (Rohm & Haas) | 000.15 |
| Triton x-100 surfactant (Astro Chemical) | 004.00 |
| Ethyl alcohol | 020.00 |
| Distilled water | 073.85 |
| Total | 100.00 |

Table E represents a list of the constituents with their CAS# for the fragrance component used in EXAMPLE 2.

TABLE E

| PRODUCT | CAS # | % |
|---|---|---|
| Aldehyde C-8 FCC | 000124-13-0 | 000.027 |
| Aldehyde C-9 FCC | 000124-19-6 | 000.027 |
| Aldehyde C-10 | 000112-31-2 | 000.027 |
| Aldehyde C-16 | 000077-83-8 | 000.884 |
| Allyl caproate FCC | 000123-68-2 | 000.135 |
| Amyl butyrate FCC | 000106-27-4 | 000.475 |
| Aubepine | 000123-11-5 | 000.046 |
| Benzyl acetate | 000140-11-4 | 000.208 |
| Benzyl alcohol | 000100-51-6 | 000.170 |
| Benzyl benzoate | 000120-51-4 | 003.543 |
| Cis-3-hexenyl acetate | 003681-71-8 | 000.004 |
| Coumarin | 000091-64-5 | 000.115 |
| Cyclamen aldehyde pure | 000103-95-7 | 001.042 |
| Delta-decalactone | 000705-86-2 | 000.054 |
| Diethyl phthalate | 000084-66-2 | 000.621 |
| Dipropylene glycol, low odor | 025265-71-8 | 054.282 |
| Ethyl butyrate | 000105-54-4 | 000.404 |

TABLE E-continued

| PRODUCT | CAS # | % |
|---|---|---|
| Ethyl maltol | 004940-11-8 | 000.075 |
| Ethyl vanillin | 000121-32-4 | 000.231 |
| Ethylene brassylate | 000105-95-3 | 000.486 |
| Geraniol bj, FCC | 000106-24-1 | 000.046 |
| Hedione | 024851-98-7 | 001.996 |
| Aquanal | 001205-17-0 | 000.083 |
| Heliotropine | 000120-57-0 | 000.185 |
| Hydroxycitronellal bj | 000107-75-5 | 002.355 |
| Cis-3-hexenol | 000928-96-1 | 000.085 |
| Lilial | 000080-54-6 | 001.042 |
| Linalool | 000078-70-6 | 001.352 |
| Lyral | 031906-04-04 | 000.695 |
| Methyl ionone gamma supreme | 001335-46-2 | 000.676 |
| Oenanthic ether | 000110-38-3 | 002.569 |
| Oxanone crystals | 005471-51-2 | 000.193 |
| Melonal | 000106-72-9 | 000.142 |
| Nonadienal | 000557-48-2 | 000.003 |
| Triplal | 027939-60-2 | 000.081 |
| Vanillin nf FCC | 000121-33-5 | 000.655 |
| Gamma-undecalactone | 000104-67-6 | 004.056 |
| Vanilla absolute | 008024-06-4 | 000.002 |
| Oil mandarin italian select | 008008-31-9 | 000.216 |
| -2, 6-nonadien-1-ol | 028069-72-9 | 000.003 |
| Lemon oil n/s | 008008-56-8 | 000.541 |
| Tagete oil | 008016-84-0 | 000.027 |
| Cognac oil, green | 008016-21-5 | 000.081 |
| Orange oil | 008008-57-9 | 002.434 |
| Dimethyl benzyl carbinyl butyrate | 010094-34-5 | 000.054 |
| Allyl amyl glycolate | 067634-00-8 | 000.041 |
| Ethyl-2-methylbutyrate, FCC | 007452-79-1 | 000.377 |
| Gamma dodecalactone | 002305-05-7 | 000.081 |
| Benzoin resin | 009000-05-9 | 000.023 |
| Cassis base 345 b | N/A | 000.270 |
| Methyl undecylenate | 000111-81-9 | 004.000 |
| Ethyl undecylenate | 000692-86-4 | 012.000 |
| Abbalide bb | 001222-05-5 & 000120-51-4 | 000.764 |
| Buccoxime | 075147-23-8 | 000.014 |
| Total | | 100.000 |

EXAMPLE 2

Consumer Preference Study Comparing Treatment of Fabrics Imbued with Different Malodors with ONP Spray Versus Commercially Available Product An odor-neutralizing pre-mix ("ONP") is prepared with fragrance components and undecylenate according to Table E, wherein the undecylenate constitutes 25% by w eight methyl undecylenate and 75% by weight ethyl undecylenate. The ONP is then added to a carrier solution according to Table D at 0% (control), 1% and 2% levels to form a test solution. A 100% cotton denim fabric is then pre-washed using an unfragranced detergent, dried and cut into 4×4 inch squares to create test fabrics. Malodor solutions consisting of a 0.1% w/w skatole in ethyl alcohol, and garlic extract, were prepared, wherein each malodor solution was placed in one of two separate pump spray units of identical configuration and make. Three sprays of each malodor solution are separately sprayed onto separate test fabrics through a 1.5 inch diameter circular stencil and allowed to dry for 3 minutes. Separate test fabrics were exposed to cigarette smoke by placing them into smoke chambers with burning cigarettes for a 20 minute time period. The 1.0% and 2.0% ONP solutions, as well as the 0% control, are then separately sprayed through a 2.0 inch diameter circular stencil onto separate dried test fabrics each having the different (i.e., skatole, garlic, cigarette smoke) malodor to ensure over spray of the malodor treated area.

Figure 2A:
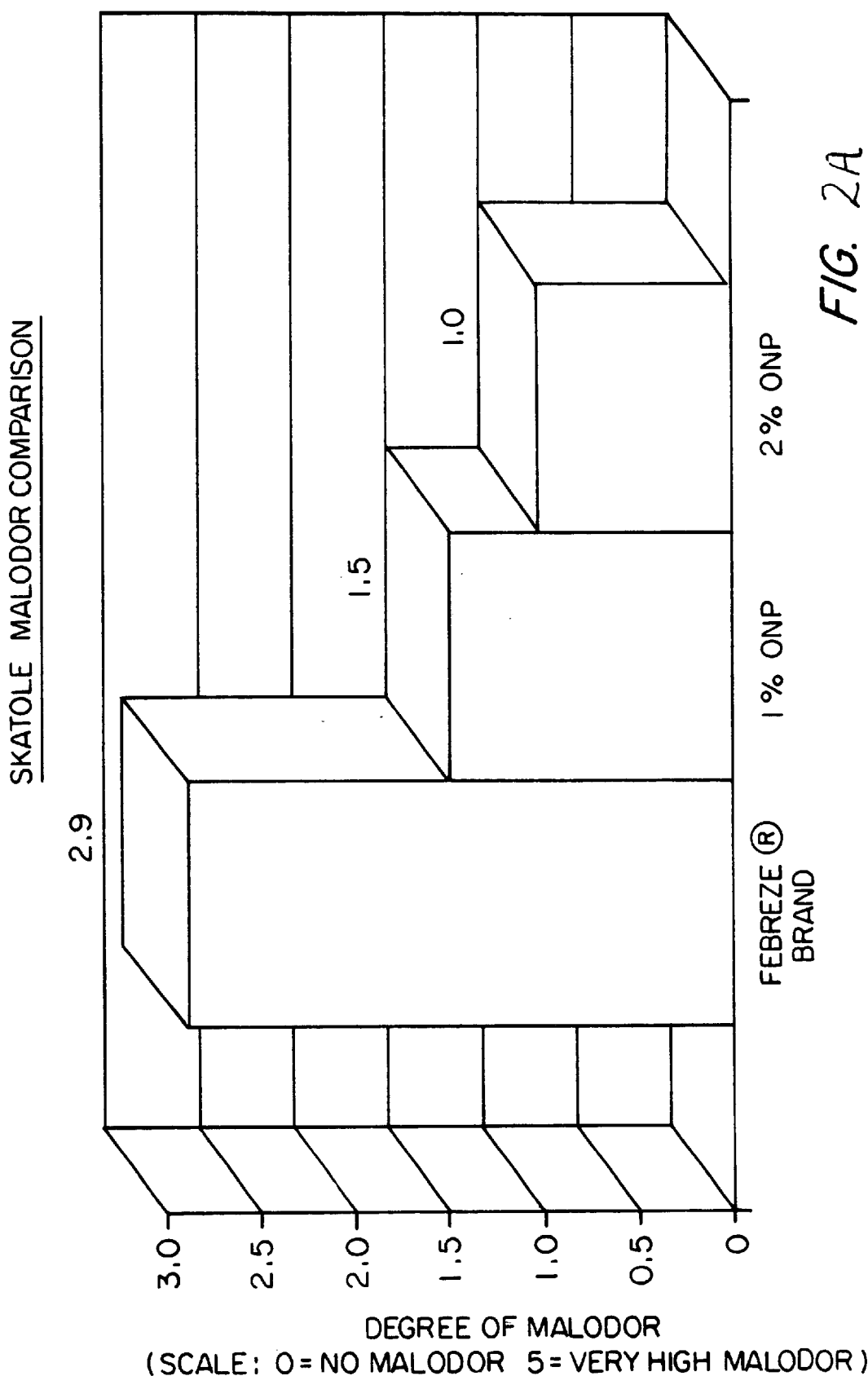
FIGS. 2A–C graphically show the consumer testing results after treatment with the composition of the present invention tested in Example 2.
Figure 2B:
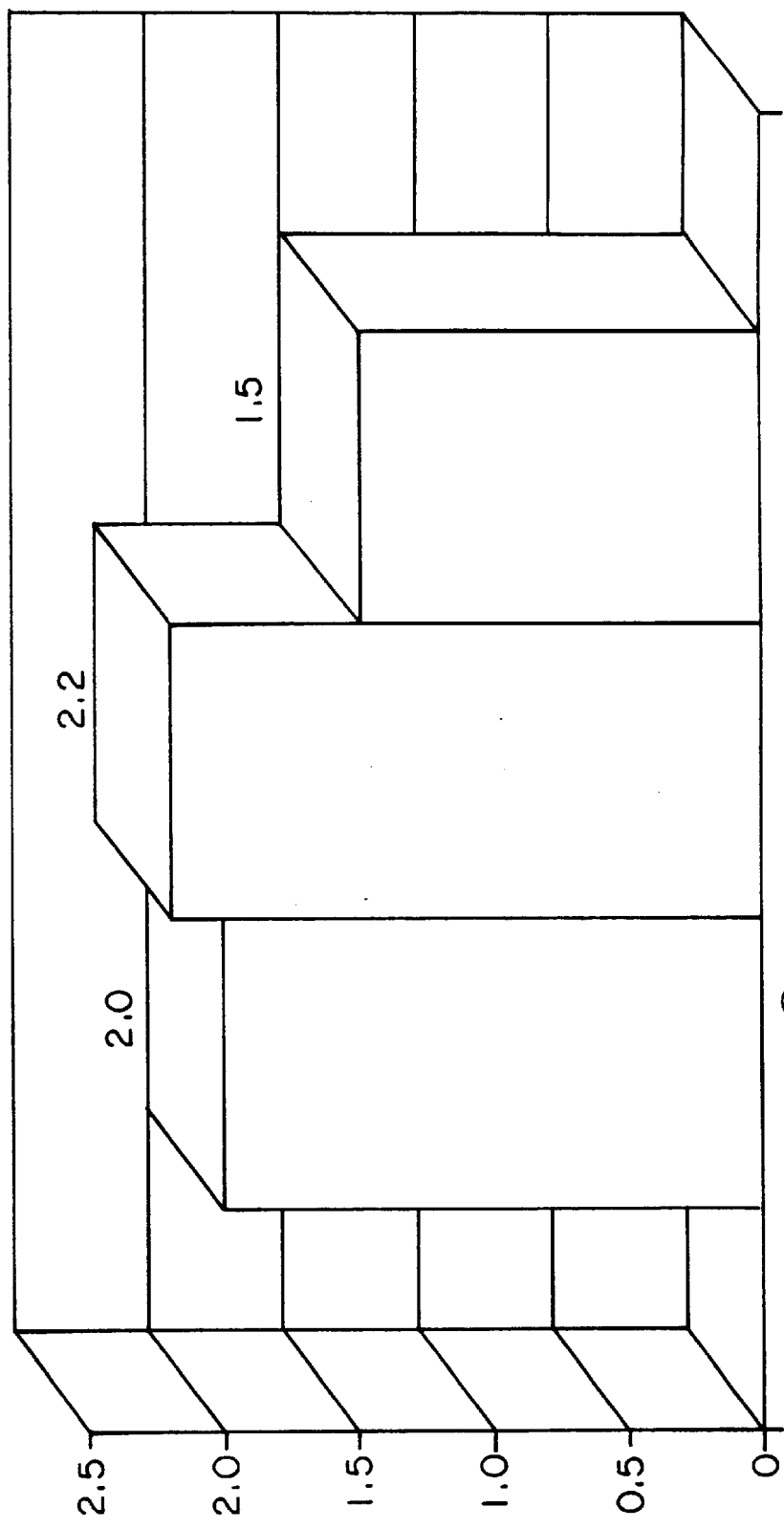
Figure 2C:
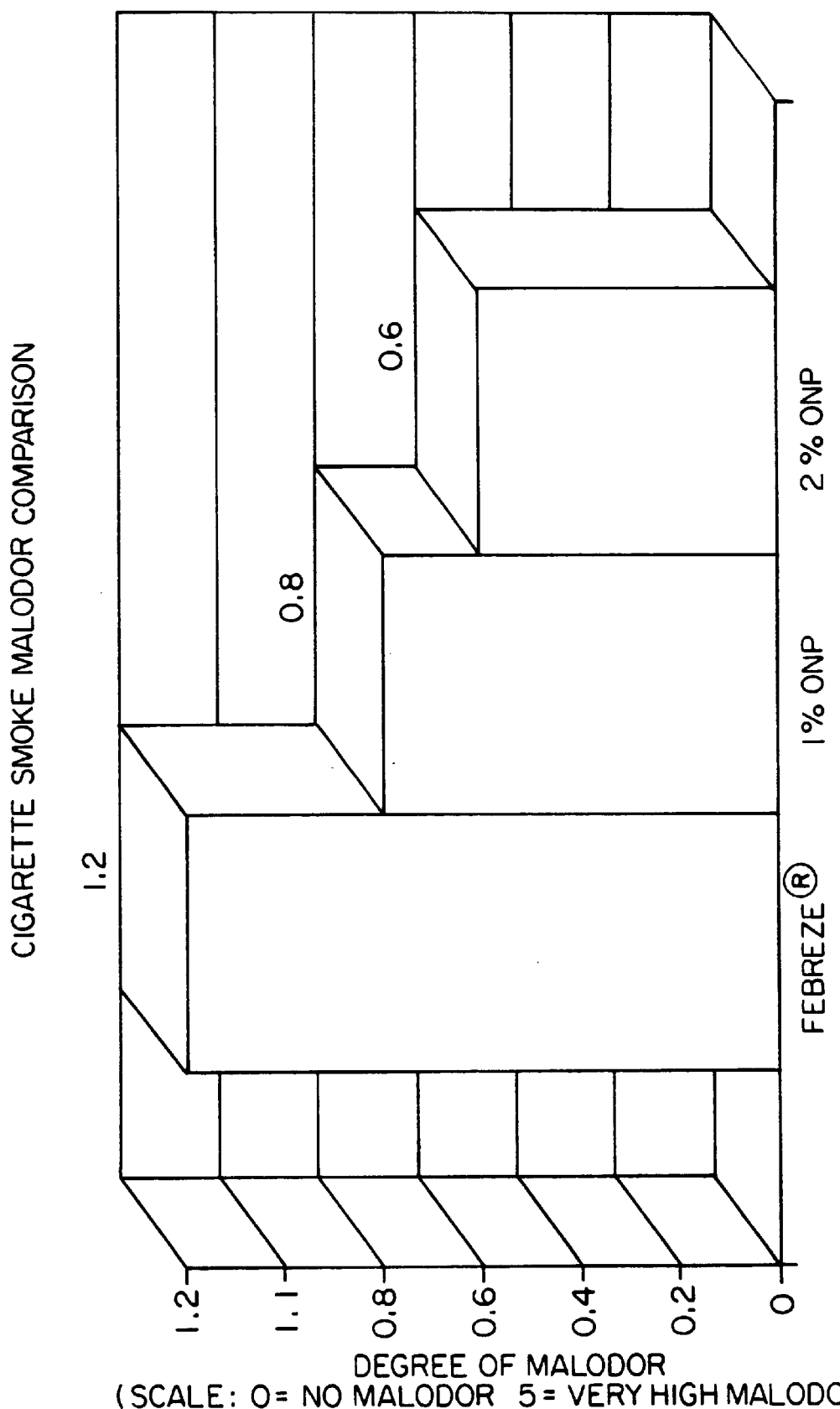

In addition, a separate test fabric for each dried malodor is also treated with 3 sprays of Febreze® odor remover as manufactured by Procter & Gamble, Inc. of Cincinnati, Ohio, in an identical manner and with an identical pump spray unit used for the 1.0%, 2.0% ONP and control solutions. Twenty-five non-smoking women between the ages of 18 and 54 were asked to rate the treated and untreated test fabrics for odor pleasantness on a five point scale (0=no malodor to 5=very high malodor). As shown in Tables 2A–2C and FIGS. 2A–2C, the ONP solutions provided considerable malodor reduction.

TABLE 2A

Skatole Comparison

| Treatment | Mean Rating |
| --- | --- |
| Control | 2.9 |
| FEBREZE ® Brand | 2.9 |
| 1% ONP | 1.5 |
| 2% ONP | 1.0 |

SCALE = 0–5

TABLE 2B

Garlic Odor Comparison

| Treatment | Mean Rating |
| --- | --- |
| Control | 3.0 |
| FEBREZE ® Brand | 2.0 |
| 1% ONP | 2.2 |
| 2% ONP | 1.5 |

SCALE = 0–5

TABLE 2C

Cigarette Smoke Comparison

| Treatment | Mean Rating |
| --- | --- |
| Control | 1.4 |
| FEBREZE ® Brand | 1.2 |
| 1% ONP | 0.8 |
| 2% ONP | 0.6 |

SCALE = 0–5

EXAMPLE 3

Figure 3:
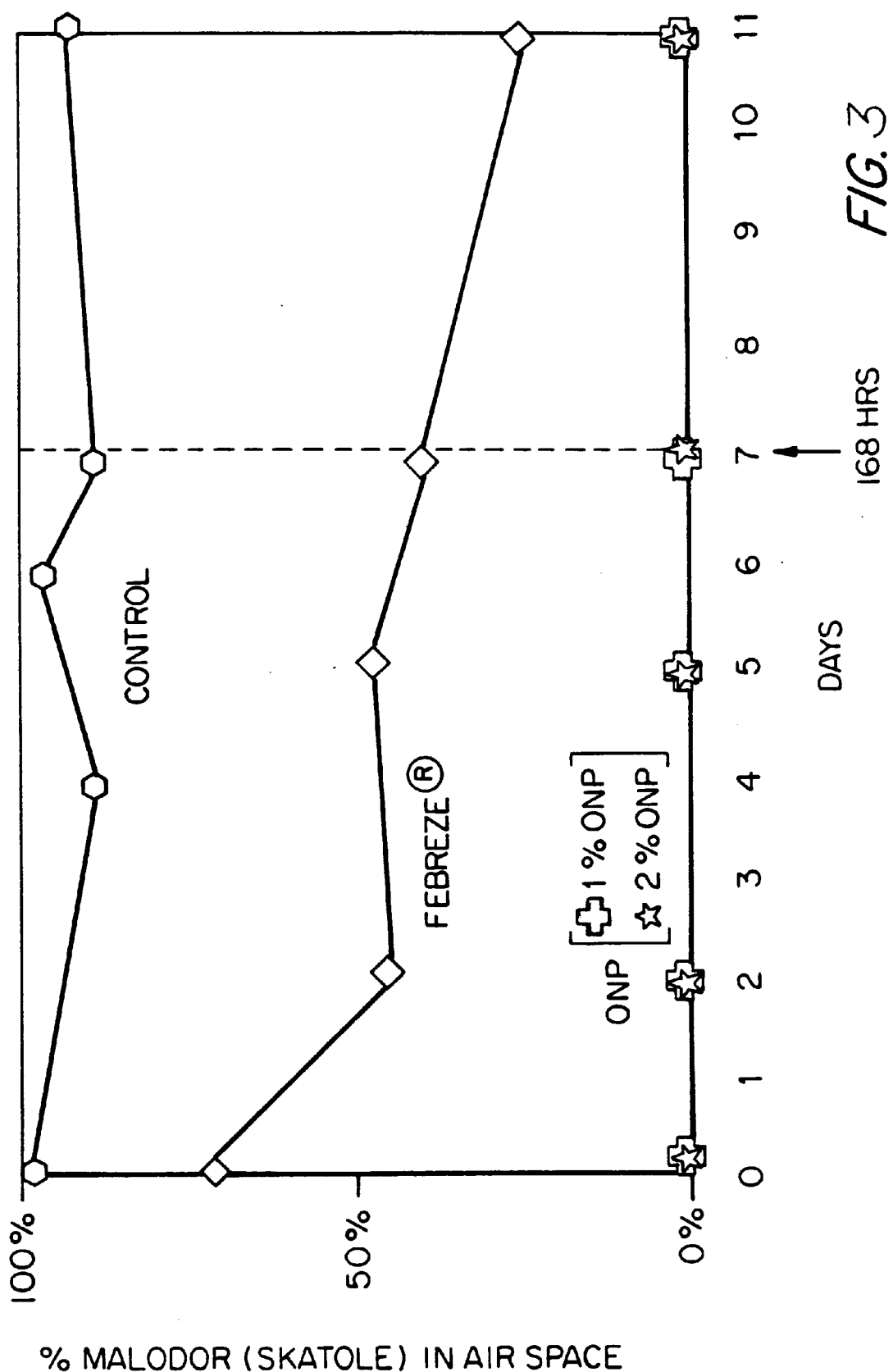
FIG. 3 graphically shows the reduction in malodor (skatole) detected in the air space after treatment with the composition of the present invention tested in Example 3 and shown in FIG. 2A.

Effectiveness of Odor-Neutralizing Agents/ Fragrance Over Time Against Skatole Malador Versus Commercially-Available Product The procedure used in this example is identical to EXAMPLE 2 except only the malodor solution consisting of a 0.1% w/w skatole solution in ethyl alcohol is used. The denim test fabrics are then placed in sealed head space vials and the headspace above the test fabrics are initially analyzed and then analyzed, 168 hours thereafter. As shown below in Table 3 and FIG. 3, ONP solutions provide considerable malodor reduction over a 168 hour period. These analytical results using SPME analysis support the consumer preference results shown in Table 2A.

TABLE 3

Percent of Skatole Detected in Air Space

| Time | Control | FEBREZE ® | 1% ONP | 2% ONP |
| --- | --- | --- | --- | --- |
| Initial | 98.0% | 70.4% | 1.0% | 1.4% |
| 168 hours | 82.4% | 34.4% | 2.3% | 3.5% |

EXAMPLE 4

Figure 4:
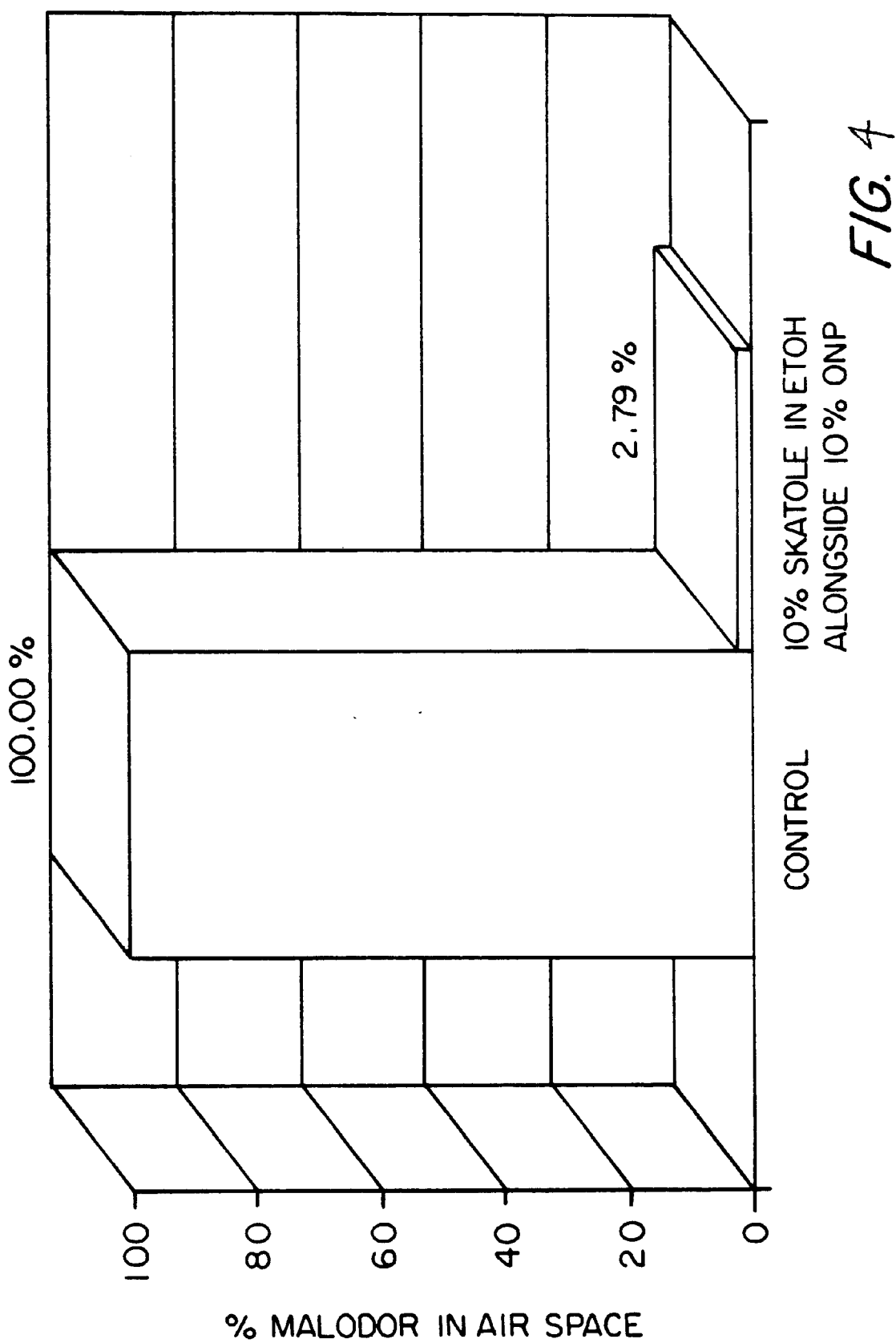
FIG. 4 graphically shows the reduction in malodor (skatole) detected in the air space after treatment with the composition of the present invention tested in Example 4.

Effectiveness of Odor-Neutralizing Agents Against Skatole Odorant When the Odor Neutralizing Agents and Malodor Are Separated and Not Mixed An odor-neutralizing pre-mix ("ONP") without fragrance components is prepared containing a 10% w/w solution of undecylenate in ethanol, wherein the undecylenate constitutes 25% methyl undecylenate and 75% ethyl undecylenate. The ONP solution is placed into an enclosed test chamber in an open beaker alongside another open beaker of 10% w/w skatole (skatole being a main component of feces smell) in ethanol, and allowed to stand for 10 minutes. These two beakers are compared to a control of 10% w/w skatole in ethanol placed into the same test chamber in an open beaker identical to that used for the ONP and 10% w/w skatole solutions. The headspace of each test chamber is sampled to determine the amount of skatole in the test chamber's air space. As shown in Table 4 and FIG. 4, the ONP solution was found to significantly reduce the percent of malodor in the air space without physical mixing or spraying.

TABLE 4

| Contents of beaker in test chamber | Percent of skatole detected in air space |
| --- | --- |
| 10% skatole in ethanol (control) | 100.00% |
| 10% skatole in ethanol alongside 10% ONP | 2.79% |

EXAMPLE 5

Figure 5:
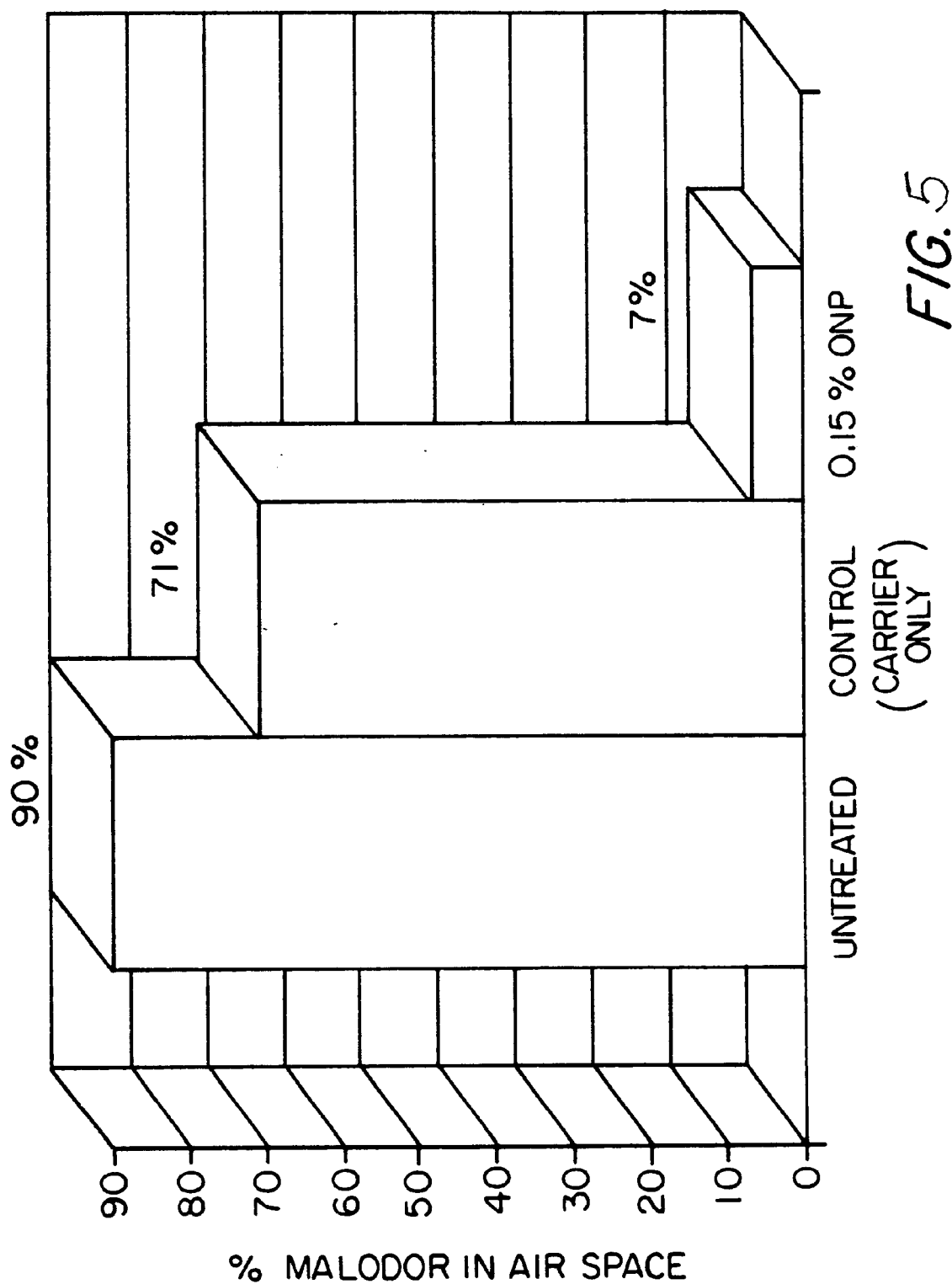
FIG. 5 graphically shows the reduction in malodor (skatole) detected in the air space after treatment with the composition of the present invention tested in Example 5.

Effectiveness of Odor-Neutralizing Agents on Treatment of Fabrics Imbued with Skatole Malodor An odor-neutralizing pre-mix ("ONP") without fragrance components is prepared containing a 0.15% w/w solution of undecylenate in an unfragranced carrier solution according to Table D, wherein the undecylenate constitutes 25% methyl undecylenate and 75% ethyl undecylenate. A 100% cotton denim fabric is then pre-washed using an unfragranced detergent, dried and cut into 4×4 inch squares to create test fabrics. A malodor solution consisting of a 0.1% w/w skatole in ethanol is separately sprayed onto separate test fabrics through a 1.5 inch diameter circular stencil and allowed to dry for 3 minutes. A control solution consisting of the carrier solution according to Table D and the 0.15% ONP solution are then separately sprayed through a 2.0 inch diameter circular stencil onto separate dried test fabrics each having the skatole malodor to ensure over spray of the malodor treated area. A separate test fabric (untreated with ONP) imbued with just 0.1% w/w skatole in ethanol, is also prepared as described above. The denim test fabrics are then placed in a sealed head space vials and the headspace above the test fabrics are analyzed. As shown in Table 5 and FIG. 5, the ONP solution was found to significantly reduce the percent of malodor in the air space.

TABLE 5

| Treatment of 0.1% Skatole Test Fabrics | Percent of skatole detected in air space |
|---|---|
| Untreated with ONP | 90% |
| Control (carrier solution only) | 71% |
| 0.15% ONP | 7% |

The above description is intended to enable the person skilled in the art to practice the invention. It is not intended to detail all possible modifications and variations which will become apparent to the skilled worker upon reading the description. It is intended, however, that all such modifications and variations be included within the scope of the invention. The claims are meant to cover the indicated elements and steps in any arrangement or sequence which is effective to meet the objectives intended for the invention, unless the context specifically indicates the contrary.

While the invention has been described with respect to preferred embodiments and examples, those skilled in the art will readily appreciate that various changes and/or modifications can be made to the invention without departing from the spirit or scope of the invention as defined by the appended claims.

What is claimed is:

1. A composition for reducing malsensory agents while allowing release of a selected component comprising:
    a component selected from the group consisting of fragrances, flavors, and mixtures thereof;
    undecylenic acid or a derivative thereof, wherein said undecylenic acid or said derivative is in an amount effective to reduce the malsensory agent and allow release of said component from the composition; and
    wherein said derivative of undecylenic acid further includes a ratio of methyl ester to ethyl ester in a range of approximately 5/95 to approximately 30/70.

2. The composition of claim 1, further comprising an alkyl ester of undecylenic acid.

3. The composition of claim 1 wherein said undecylenic acid or derivative is about equal in ratio to the weight percent of said component.

4. The composition of claim 1 wherein said undecylenic acid or derivative is about 50% of the weight percent of said component.

5. The composition according to claim 1, wherein the composition further comprises approximately 0.005%–50% undecylenic acid or a derivative thereof, wherein said undecylenic acid or said derivative is in an amount effective to reduce the malsensory agent and allow release of said component from the composition.

6. The composition according to claim 1, wherein the composition further comprises approximately 0.1%–4% undecylenic acid or a derivative thereof, wherein said undecylenic acid or said derivative is in an amount effective to reduce the malsensory agent and allow release of said component from the composition.

7. The composition according to claim 6, wherein the composition comprises approximately 0.005%–1.2% by weight methyl ester.

8. The composition according to claim 6, wherein the composition comprises approximately 0.07%–3.8% by weight ethyl ester.

9. The composition according to claim 1, wherein the composition comprises approximately 0.05%–95% fragrances, flavors, and mixtures thereof.

10. The composition according to claim 1, wherein the composition comprises a ratio of uyndecylenic acid to fragrance in the range of approximately 0.005/95 to approximately 50/0.05.

11. A composition for reducing malsensory agents while allowing release of a selected component comprising:
    a component selected from the group consisting of fragrances, flavors, and mixtures thereof; and
    undecylenic acid or a derivative thereof, said undecylenic acid or derivative being in a ratio of methyl ester to ethyl ester from about 5:95 to about 30:70 by weight wherein said undecylenic acid or derivative is in an amount effective to reduce the malsensory agents and allow release of said component from the composition.

12. A final product comprising the composition of claim 11, wherein the composition is contained in a product selected from the group consisting of a candle, carpet care product, bathroom care product, baby care product, deodorant, antiperspirant, feminine hygiene product, air freshener, perfume, cologne, adult incontinence product, fabric/laundry product, oral hygiene product, household cleaning product, hair care product, hand cleaners, wipes, breath fresheners, depilatories, insecticides and repellents.

13. A solid-state composition for reducing malsensory agents while allowing release of a selected component from the composition comprising:
    a substrate having a surface for depositing a composition thereon;
    a component selected from the group consisting of fragrances, flavors, and mixtures thereof;
    undecylenic acid or a derivative thereof, wherein said undecylenic acid or said derivative is in an amount effective to reduce the malsensory agent and allow release of said component from the composition; and
    wherein said derivative of undecylenic acid further includes a ratio of methyl ester to ethyl ester in a range of approximately 5/95 to approximately 30/70.

14. A method for using a composition having undecylenic acid or a derivative thereof in a final product to reduce malsensory agents comprising the step of:
    applying the composition having undecylenic acid or a derivative thereof to the final product in an amount effective to reduce the malsensory agents and allow release of a component from the composition, wherein said component is selected from the group consisting of fragrances, flavors, and mixtures thereof;
    wherein said derivative of undecylenic acid further includes a ratio of methyl ester to ethyl ester in the range of approximately 5/95 to approximately 30/70.

15. The method of claim 14 wherein the applying step further comprises mixing a component selected from the group consisting of fragrances, flavors, and mixtures thereof with undecylenic acid or a derivative thereof to form a odor neutralizing pre-mix, wherein said pre-mix is applied to the final product.

16. The method of claim 14 wherein said derivative of undecylenic acid further includes a ratio of methyl ester to ethyl ester in a range of approximately 5/95 to approximately 30/70.

17. The method of claim 14 wherein the composition is in solution, suspension, emulsion, foam, granule, gel, aerosol, non-aerosol, microencapsulated, plastic, polymer or powder form.

* * * * *

UNITED STATES PATENT AND TRADEMARK OFFICE
CERTIFICATE OF CORRECTION

PATENT NO. : 6,495,097 B1
DATED : December 17, 2002
INVENTOR(S) : Allan L. Streit et al.

It is certified that error appears in the above-identified patent and that said Letters Patent is hereby corrected as shown below:

Title page,
Item [73], should read -- [73] Assignee: Shaw Mudge & Company, Shelton, CT (US) --

Column 10,
Line 49, change "w eight" to -- weight --.

Signed and Sealed this

Sixth Day of May, 2003

JAMES E. ROGAN
*Director of the United States Patent and Trademark Office*